United States Patent [19]  
Kulisz et al.

[11] Patent Number: 5,000,739  
[45] Date of Patent: Mar. 19, 1991

[54] PROGRAMMABLE INFUSION PUMP

[75] Inventors: Andrzej Kulisz, Moundsview; Robert Kendig, Coon Rapids; Jeffrey Williams, Moundsview, all of Minn.

[73] Assignee: Pinewood Medical, Inc., Moundsview, Minn.

[21] Appl. No.: 218,110

[22] Filed: Jul. 12, 1988

[51] Int. Cl.⁵ .............................................. A61M 5/00
[52] U.S. Cl. .................................... 604/132; 604/153; 604/216; 604/246; 128/DIG. 12
[58] Field of Search ............... 604/246, 132, 153, 154, 604/155, 131, 133, 403, 216; 128/DIG. 12, DIG. 13; 222/386.5, 390, 333, 206, 215

[56] References Cited  
U.S. PATENT DOCUMENTS

| | | | |
|---|---|---|---|
| 3,017,883 | 1/1962 | Dickinson | 604/415 |
| 3,623,474 | 11/1971 | Heilman et al. | 604/155 |
| 4,217,897 | 8/1980 | Sneider | 604/216 |
| 4,634,430 | 1/1987 | Polaschegg | 604/153 |

Primary Examiner—Pellegrino Stephen C.  
Attorney, Agent, or Firm—Hugh D. Jaeger

[57] ABSTRACT

A programmable pump with three separate components: a driver, a reservoir and a tubing set connector. The driver provides an electromechanical assembly causing fluid to flow from the reservoir. The driver can be programmed for varying flow rates and alternating on/off delivery cycles through the control of switches externalized on the driver face. The reservoir is designed as a separate component. The driven side of the reservoir is the bottom. The top of the reservoir includes a port, and the bottom includes a septum for filling by a needle. The tubing set connector subsequently mounts into the port connector of the reservoir. The tubing set connector provides the interface to any standard luer-type tubing set which then connects to a needle for infusion. The circuitry is hardware logic programmable circuitry.

19 Claims, 13 Drawing Sheets

PROGRAMMABLE INFUSION PUMP

CROSS REFERENCES TO CO-PENDING APPLICATIONS

None.

BACKGROUND OF THE INVENTION

1. Field of the Invention

The present invention relates to a medical drug pump, and more particularly, pertains to a hardware programmable infusion pump.

2. Description of the Prior Art

Presently the market potential for drug infusion pumps and services approaches $350 million per year, and is experiencing an annualized growth rate of 25-30%. Several major medical device companies have representation in this facet of the business, and the sales are spread across several competitors.

The present move towards health care cost containment has caused a great deal of price versus feature analysis in the purchase decisions for infusion pumps and related products. Additionally, products that decrease nursing time or facilitate drug delivery on an out-patient basis are experiencing a greater growth rate in sales. Infusion pumps generally are durable medical products, and are expensive, require nursing time to manage inventory and to refill, need repair, and cause additional cost in service contracts. The additional cost is passed on to the patient and ultimately to the third party insurance carrier.

There are currently two companies that provide disposable pumps for drug delivery. Travenol markets a balloon reservoir in a cartridge called the Infusor, and ISC markets a similar product. The balloon or bladder of Travenol has prestressed walls and when filled with a drug solution, delivers the solution with reasonable accuracy over approximately 24 hours. Neither device is programmable and costs approximately $30 per day. The major use of these devices is in cancer therapy, where a typical treatment cycle lasts at least five days resulting in at least $150 in pump costs. Secondly, the need for daily replacement adds nursing time and nursing expense.

The present invention provides a low-cost programmable disposable infusion pump that is intended for use in medical therapy where there is a continuous or recurrent need for drug delivery. The pricing of the pump in the marketplace, along with certain design features, provides the pump as a limited use device. Such diseases or disorders include cancer, chronic infections, cardiovascular and hematological diseases, severe pain and neurological disorders and diabetes. The pump is designed for single use in delivering 20–250 ml of drug solution over an undefined period of time. The product can be priced and marketed as a single-use programmable infusion pump or can be used as a multi-use programmable infusion pump.

SUMMARY OF THE INVENTION

The general purpose of the present invention is a low-cost drug infusion pump intended for use in medical therapy. The product is disposable after single or limited use. Delivery of a drug is from a reservoir of 20 to 250 ml of solution over the time of 30 days or less. The length of use will be determined by the volume of the reservoir, flow rate, time on, and time off of delivery.

The pump incorporates several features which currently only exist in products designed for re-use in the hospital or clinic, and which are found significantly more expensive of the $1,800–$3,000 price range.

In order for these durable pumps to be competitive, the pumps must be programmable and adjustable in delivery rates to satisfy a number of therapeutic needs.

Such a pump must be reliable and precise in meeting the delivery needs. The pump must be fail-safe and carry a number of safeguards which prevent the pump from causing harm to the patient. The pump must deliver as programmed, and alarm the patient of any malfunction. The pump must discontinue operation and shut down if the magnitude of malfunction is beyond the patient's ability to correct it. The pump must also discontinue operation if the patient does not react to the alarm within the required time and manner.

The pump is designed as three separate components; the driver assembly, the reservoir and the tubing set connector.

Driver: The driver is a mechanical assembly, electrically powered, and electronically controlled. Its function is to actively pump the drug from the reservoir. It consists of two primary parts; the electronic/mechanical assembly that the reservoir mounts into, and a protective cover that encloses the mounted reservoir. The displacement of reservoir volume is achieved by a direct drive linear actuator, where a threaded shaft moves axially as advanced by the rotor of the actuator motor. The electronic circuitry controls the position of the shaft and advances the shaft by the energizing and activating the actuator motor. Advances are extremely small and repeatable with a high degree of resolution. The driver can be programmed to deliver the drug automatically per prescription requirements through the manipulation of selector switches located on the face plate of the housing.

Reservoir: The reservoir is a separate component that can be manufactured in different sizes, and engages with the driver in the housing to comprise the pump. The reservoir is filled by a pharmaceutical manufacturer, such as under a licensing agreement, or by a hospital pharmacist prior to use. The reservoir is molded from an inert or like plastic material and has a plurality of thin pre-formed bellow accordionlike walls to facilitate compression. The top and bottom portions of the reservoir include provisions for mounting into the driver. In the alternative, a bladder in the hard shell could be another version of the reservoir that could be used with the driver. The driven side of either reservoir will be the bottom, and the top will have a port through which the reservoir is filled. A septum is included for injections of a liquid to reconstitute powdered drugs. The tubing set connector is subsequently mounted into the port.

Connector: The tubing set connector provides the interface to any standard luer-type tubing set, which then connects to a needle for infusion. The connector and reservoir port mates in a non-reversible threaded ratcheting mechanism to provide a permanent, hermetic seal at the reservoir port exit.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
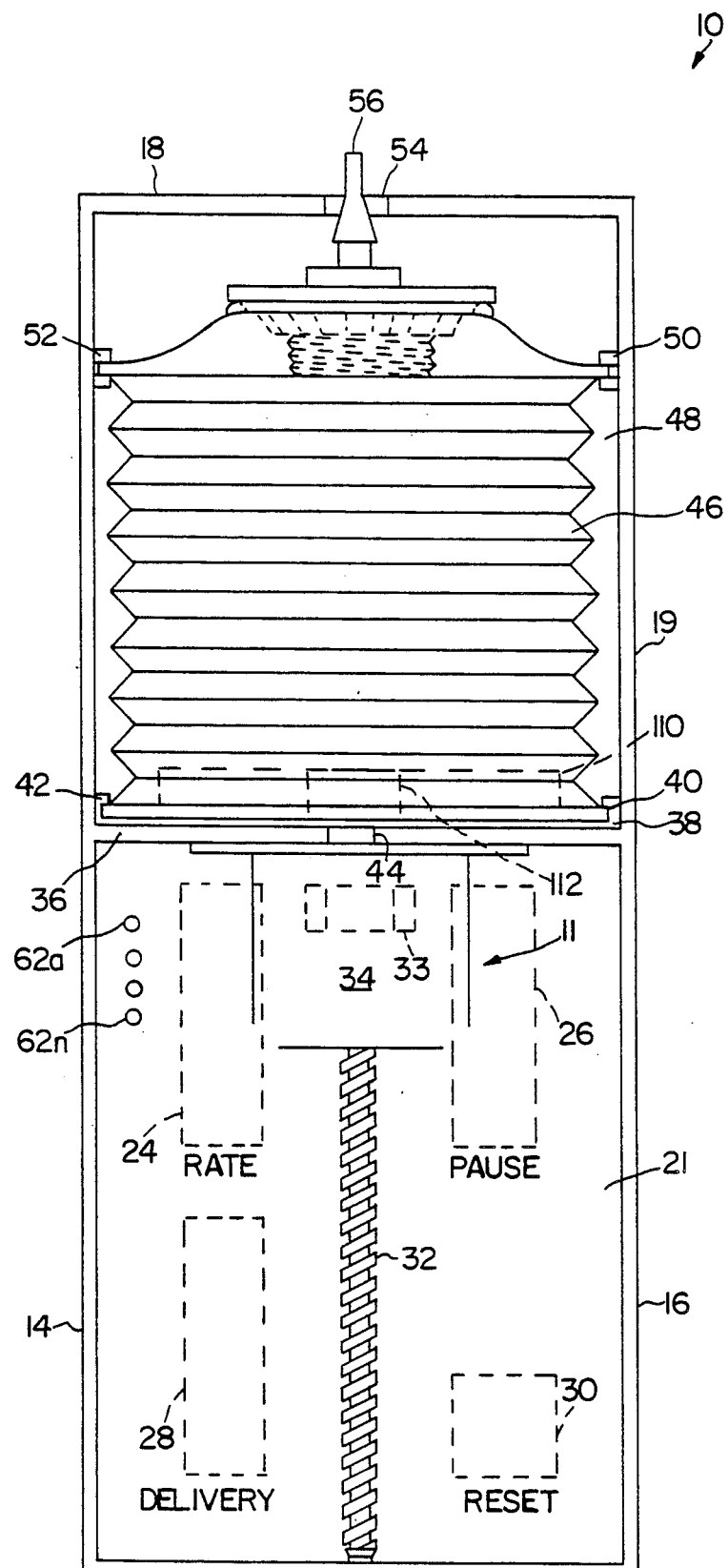
FIG. 1 illustrates a front view in cross section of a programmable, disposable infusion pump.
Figure 2:
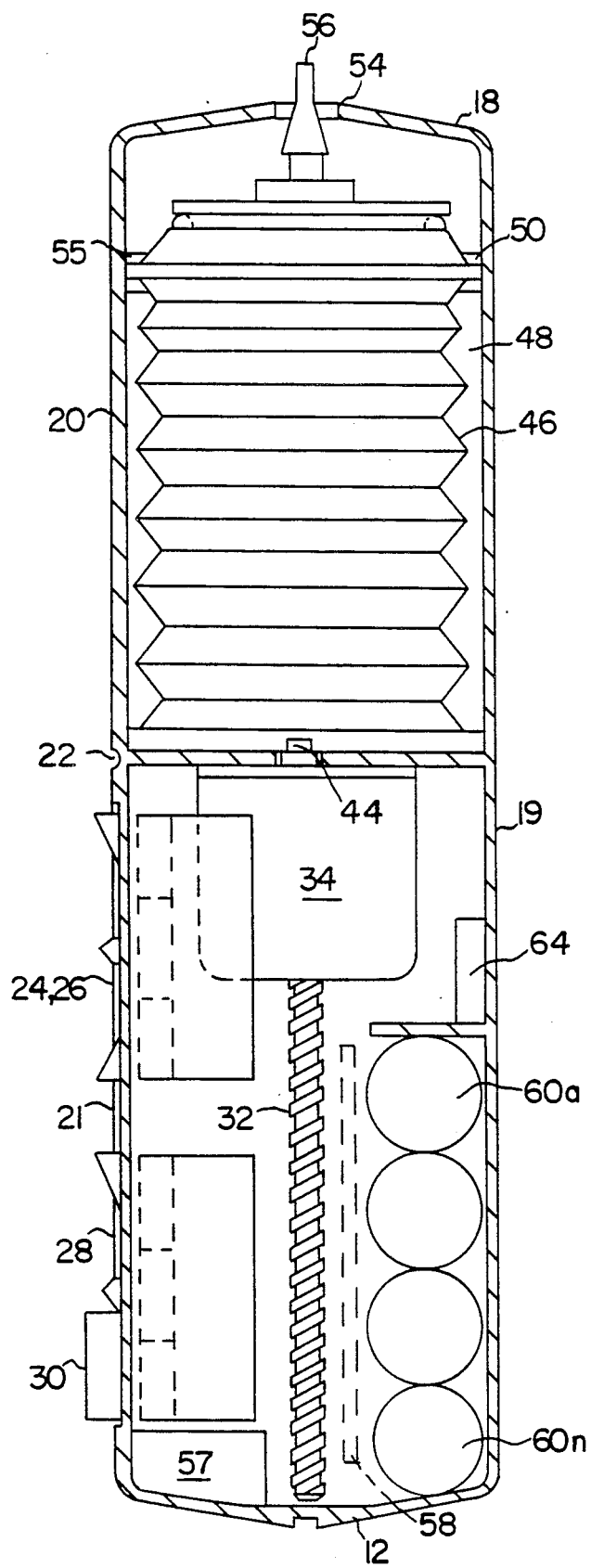
FIG. 2 illustrates a side view in cross section of the programmable, disposable infusion pump.

FIG. 1 illustrates a front view of a programmable, disposable infusion pump 10 including a case bottom 12, case sides 14 and 16, and a case top 18 of a housing 19. A snap shut door 20 on a hinge 22 is illustrated in FIG. 2. Four switches 24, 26, 28, and 30, as labeled, position on the front panel 21. The driver section 11 mounts in a lower portion of the housing 19 and includes an advancing screw shaft 32 is moved by a rotor 33 through a digital linear actuator motor 34 each of which is a member of the driver. A plate 36 divides the lower portion of the housing from the upper portion of the housing. A reservoir mounting plate 38 with flanges 40 and 42 positions above the plate 36. The advancing screw shaft 32 extends through a rotor 33 and through a hole 44 in the plate 36 and provides upward movement of the reservoir mounting plate 38 as later described. The shaft's linear upward movement is controlled by rotating components in the motor as the shaft itself does not physically rotate and moves only upward. The reservoir 46 is positioned in an upper portion of the housing in a reservoir compartment 48 and is further described in FIGS. 6 and 7. Channels 50 and 52 position in the reservoir compartment 48 to secure the top portion of the reservoir 46 within the reservoir compartment 48. Hole 54 is provided for the tubing set (catheter) connector assembly 56, as later described in detail. The reservoir is illustrated as being rectangular and can assume any other geometrical configuration for engaging and indexing into the housing.

FIG. 2 illustrates a side view in cross section of the programmable, disposable infusion pump 10 where all numerals correspond to those elements previously described. The housing includes electronic circuitry board 58, batteries 60a–60n, control indicator lights 62a–62n of FIG. 1, and an alarm buzzer 64.

Figure 3:
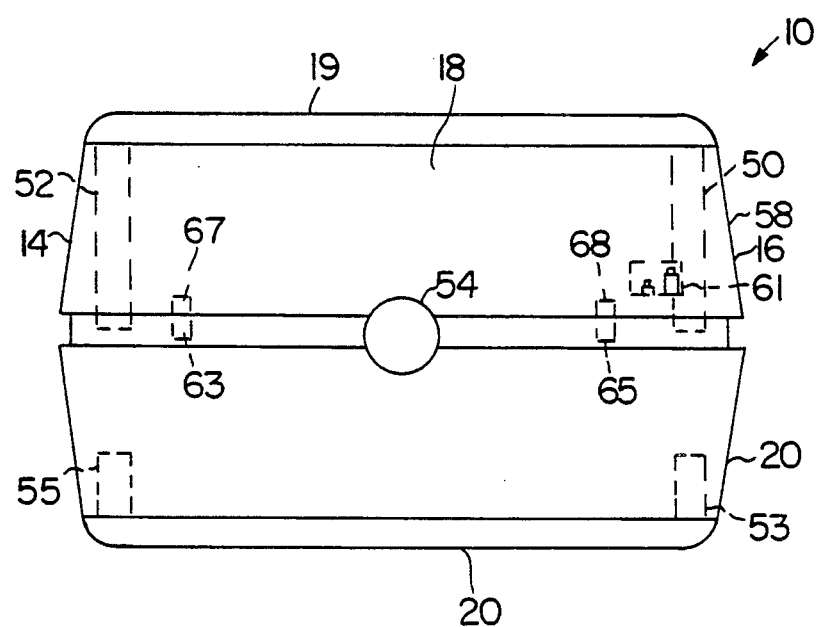
FIG. 3 illustrates a top view of the programmable, disposable infusion pump.

FIG. 3 illustrates a top view of the programmable, disposable infusion pump 10 including hooks 63 and 65 and latches 67 and 68 where all numerals correspond to those elements previously described. Channels 53 and 55 correspond to channels 50 and 52 of FIG. 1 for engagement with reservoir mounting flanges 107 and 108. Mounting flanges 107 and 108 are illustrated in FIG. 6.

Figure 4:
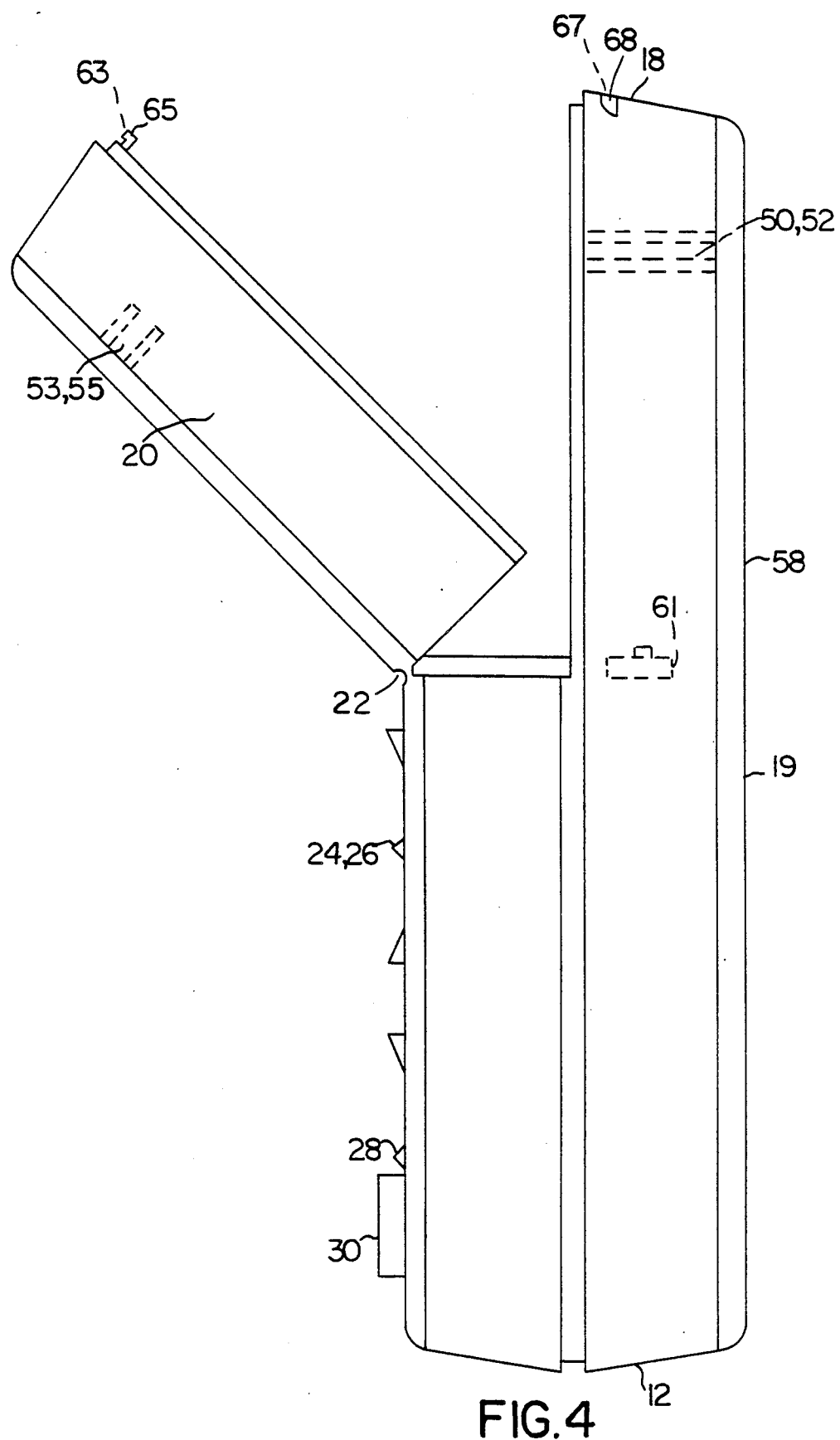
FIG. 4 illustrates a side view of the housing prior to insertion of a reservoir and closing of the snap shut door.

FIG. 4 illustrates a side view of the housing 19 prior to insertion of a reservoir 46 and closing of the snap shut door 20 where all numerals correspond to those elements previously described. A mode select switch 61 is set prior to the insertion of the reservoir 46. While a snap shut door 20 has been illustrated, in the alternative, it is in the teachings of the present invention that the door can also be opened if the pump is not utilized as a single use pump.

Figure 5:
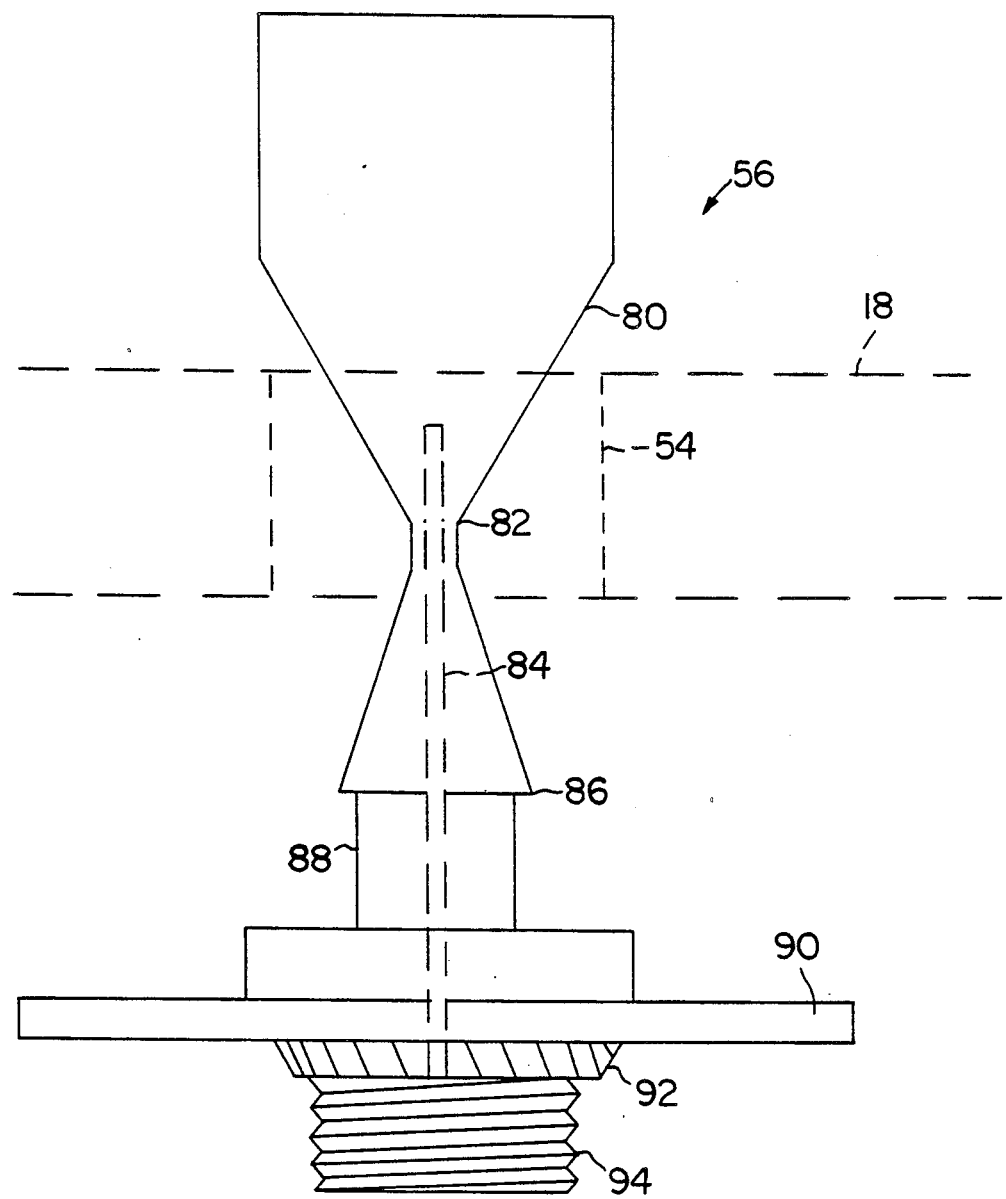
FIG. 5 illustrates a side view of the tubing set connector.

FIG. 5 illustrates a side view of the tubing set (catheter) connector assembly 56 where all numerals correspond to those elements previously described. Included from top to bottom are a breakaway tab 80, a breakaway point 82, an internal drug pathway 84 through the connector, at least one catheter tube ridge 86, a catheter connector body 88, a flange 90, a toothed ratchet surface 92 and screw threads 94. The reservoir also includes a like ratchet toothed surface as later described in detail.

Figure 6:
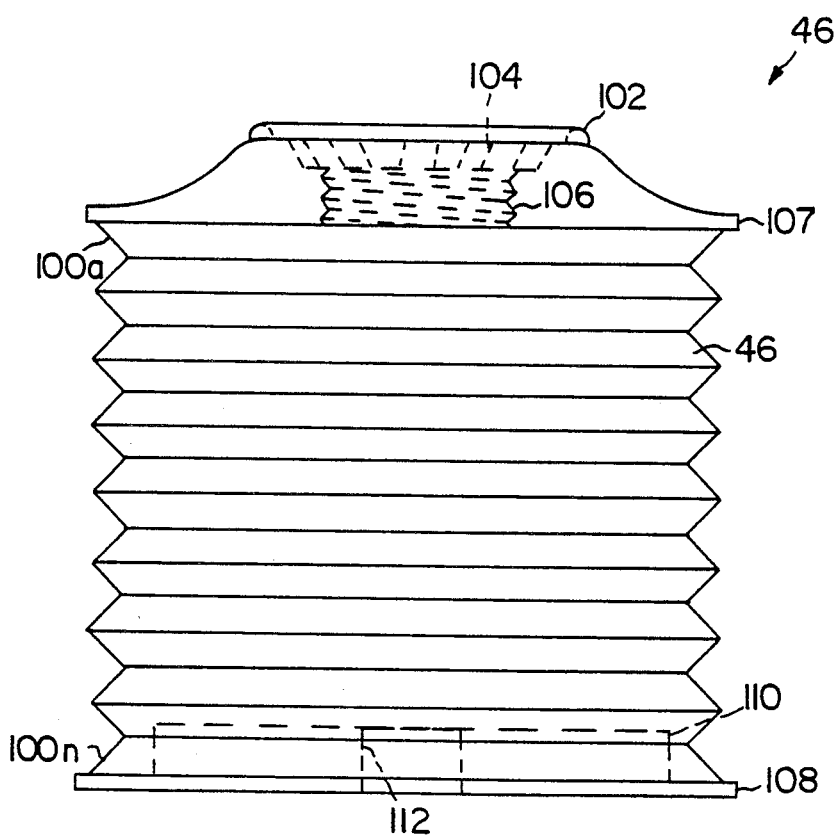
FIG. 6 illustrates a side view of the drug reservoir.

FIG. 6 illustrates the reservoir 46 including a plurality of bellows 100a–100n where all numerals correspond to those elements previously described. The reservoir 46 can be made in any configuration, but is shown as being rectangular in FIG. 7 by way of example and not to be construed as limiting. The reservoir 46 includes, in order, an annular seal 102, a reservoir ratchet tooth surface 104 to engage with the teeth of the tubing set (catheter) connector assembly 56, a threaded hole 106, an upper reservoir mounting flange 107, a lower reservoir mounting flange 108, an internal pad 110, and a septum 112 for filling by a needle if such is preferred.

Figure 7:
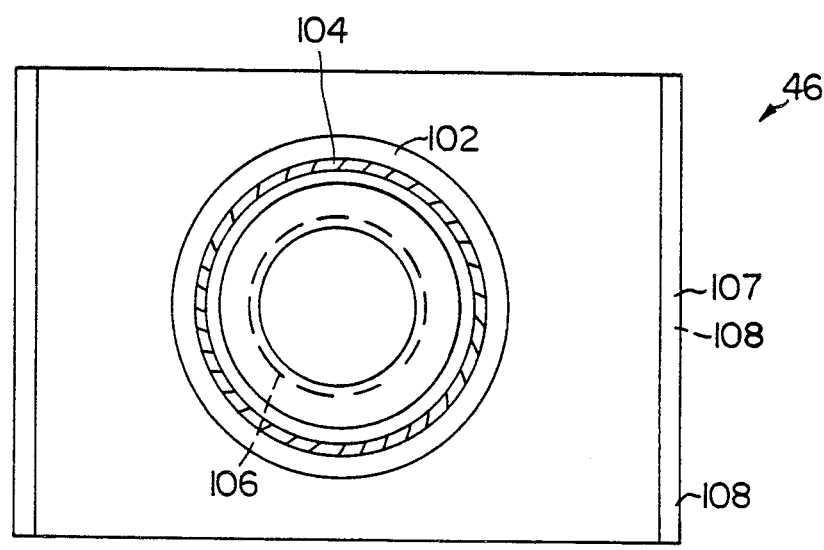
FIG. 7 illustrates a top view of FIG. 6.

FIG. 7 illustrates a top view of FIG. 6 where all numerals correspond to those elements previously described. The reservoir 46 can also be made in a circular or any other configuration.

Figure 8:
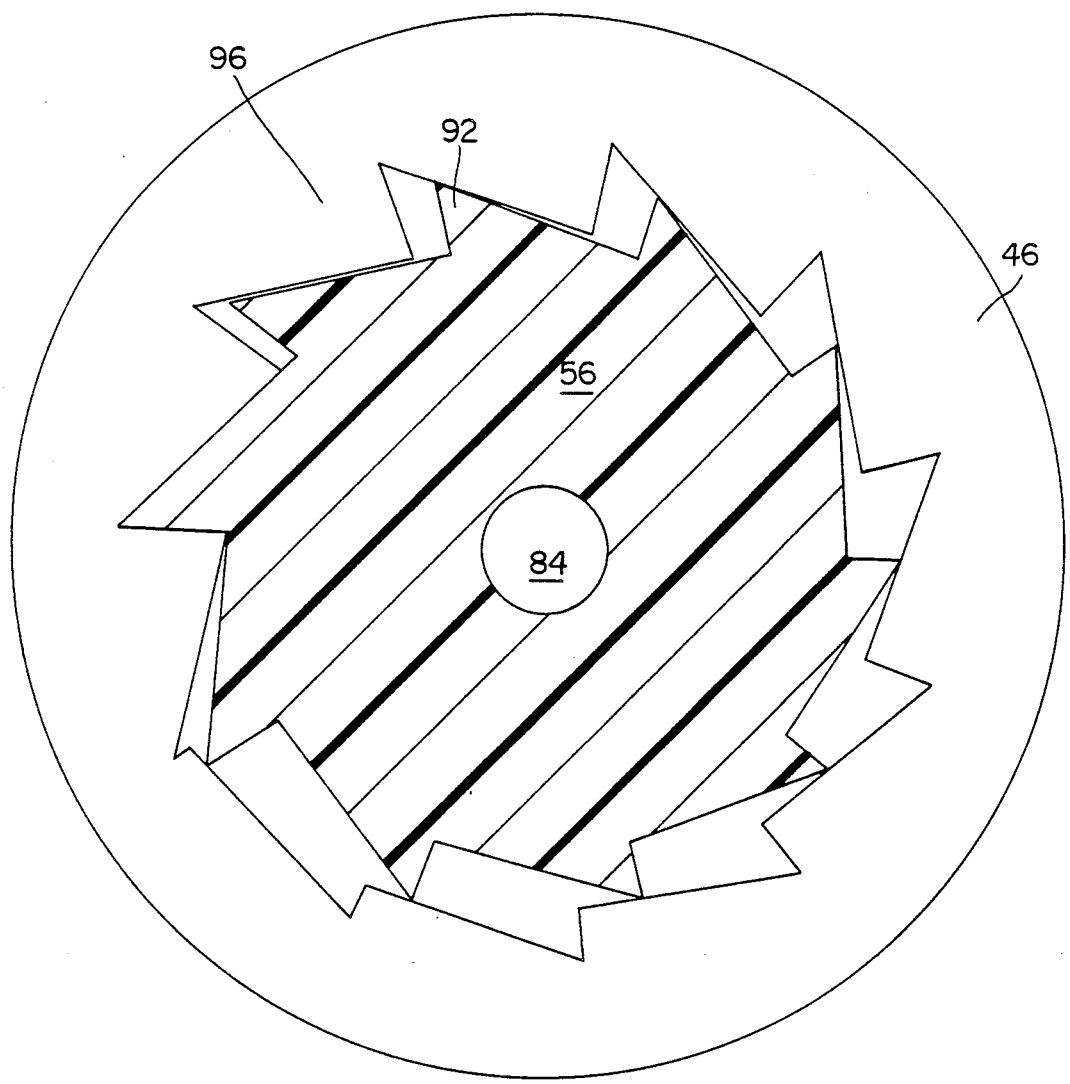
FIG. 8 illustrates a top view of the mode of teeth engagement.

FIG. 8 illustrates a top view of the mode of teeth engagement. Prior to use of the programmable, disposable infusion pump 10, a reservoir 46 is filled with a drug. The drug can either be a powder and mixed with fluid, or in the alternative, can be a liquid. A pharmaceutical company or pharmacist (doctor) would take a reservoir from a sterile package, add either a powder and/or a liquid, and then take a connector from a sterile package and screw the connector into the reservoir. By doing so with the ratcheting of the teeth, sterility is provided in that the reservoir cannot be reopened. This provides a one-way positive lock when the catheter connector is threaded onto the top of the reservoir. The number of "n" teeth 96 is molded into the top of the reservoir where the catheter connector mates with the reservoir. The teeth 92 molded into the catheter connector are in a quantity of "n+1". As the tubing set (catheter) connector assembly 56 is screwed into the top of the reservoir 46, the toothed ratchet surface 92 and n teeth 96 ratchet across each other until maximum compression of the tubing set (catheter) connector assembly and the top of the reservoir is achieved. At this point, the tubing set (catheter) connector assembly 56 cannot be tightened anymore, nor can it be loosened because of the positive lock achieved by the intermeshed teeth.

This combination of the "n" and "n+1" ensures no back turning as one tooth is always interlocked with another. This further maintains the initial seal produced by the compression mating surfaces, guaranteeing a sterile field required for the drug filled reservoir. Any forced removal of the tubing set (catheter) connector assembly causes irreparable and undeniable damage to the reservoir, prohibiting any reuse of a single cycle reservoir.

MODES OF OPERATION

Programming Modes

The device operation is split into three separate operational modes as selected by the mode select switch 61 located in the reservoir compartment 48. The modes are each specific to a delivery regimen as dictated by the user or the prescriber. The modes are:

I. t.P.A. (Tissue Plasminogen Activator) This mode serves a sequential delivery scheme required by the manufacturer of the drug tPA. When selected and activated, the pump outputs the required amounts of drug over a 3-6 hour period and then shuts off.

t.P.A. Mode of Operation

1. The device has a program mode select switch 61 located in an area that can be accessed only by the physician, ER technician, or paramedic.
2. The mode select switch 61 is positioned to t.P.A.
3. The reservoir 46 and tubing set (catheter) connector assembly 56 is attached to a catheter and is placed into the reservoir compartment 48 and the snap shut door 20 snapped into place. Access to mode control switch 61 is now possible only by destroying housing 19.
4. Pump is now ready to start t.P.A. therapy.
5. Pump will now provide 100 ml over 3-6 hours time in 4 steps.

For example:
a. Step 1: 6 ml delivered in first two minutes.
b. Step 2: 54 ml delivered over next 58 minutes.
c. Step 3: 20 ml delivered over next 60 minutes.
d. Step 4: 20 ml delivered over next 60 minutes.

6. At the end of the program duration, the pump will shut off and the alarm will sound.

II. P.C.A. (Patient Controlled Analgesia) This mode incorporates more of the programmable features of the pump by allowing the doctor to input a prescribed delivery sequence. With the pump 10 in its programming cradle, the doctor programs the basic rate and time over which the drug will be delivered at that rate, and the off interval. The doctor then removes the pump from the cradle and starts the pump for their first delivery cycle. Only after the cycle has ended, the patient may restart the original prescribed delivery cycle. As long as the device is not installed on its programming cradle 200 of FIG. 11, the device will not respond to changes of the programming switches, thus restricting the patient from altering the doctors original programmed delivery cycle.

P.C.A. Mode of Operation

1. The device has a program mode switch 61 located in an area that can be accessed only by the physician.
2. The mode select switch 61 is positioned to P.C.A. by the physician.
3. The reservoir 46, tubing set (catheter) connector assembly 56, and an attached catheter is placed into the reservoir compartment 48 and the snap shut door 20 snapped into place. Access to mode select switch 61 is now possible only by destroying the housing.
4. The pump is now placed into the cradle for programming the rate, on, and pause (off) parameters using the respective programming switches 24, 26, and 28.
5. Reset is now pushed to start delivery and the device is removed from the cradle. The program is now locked in.
6. Reset is now locked out for the duration of the programmed interval, which is the sum of the time on and pause selects.
7. At end of program duration, the pump will idle at KVO and enable reset for patient to administer programmed sequence again. KVO—Keep Vein Open—subpharmacological rate of delivery to mechanically keep vein open (low flow flush preventing occlusion of the catheter's tip).

III. General Purpose Modes. When selected, the device can use all of the available programming, except tPA, and can be changed at will by the user by changing the rate, on and off times and pressing the reset button 30. If the reset button 30 is not pressed, the changes will be executed on the next delivery cycle. Three thumbwheel switches 24, 26 and 28 of 0-9 positions set rate, pump on time, and pump off time. A reset button 30 starts or resets the pump.

Figure 9A:
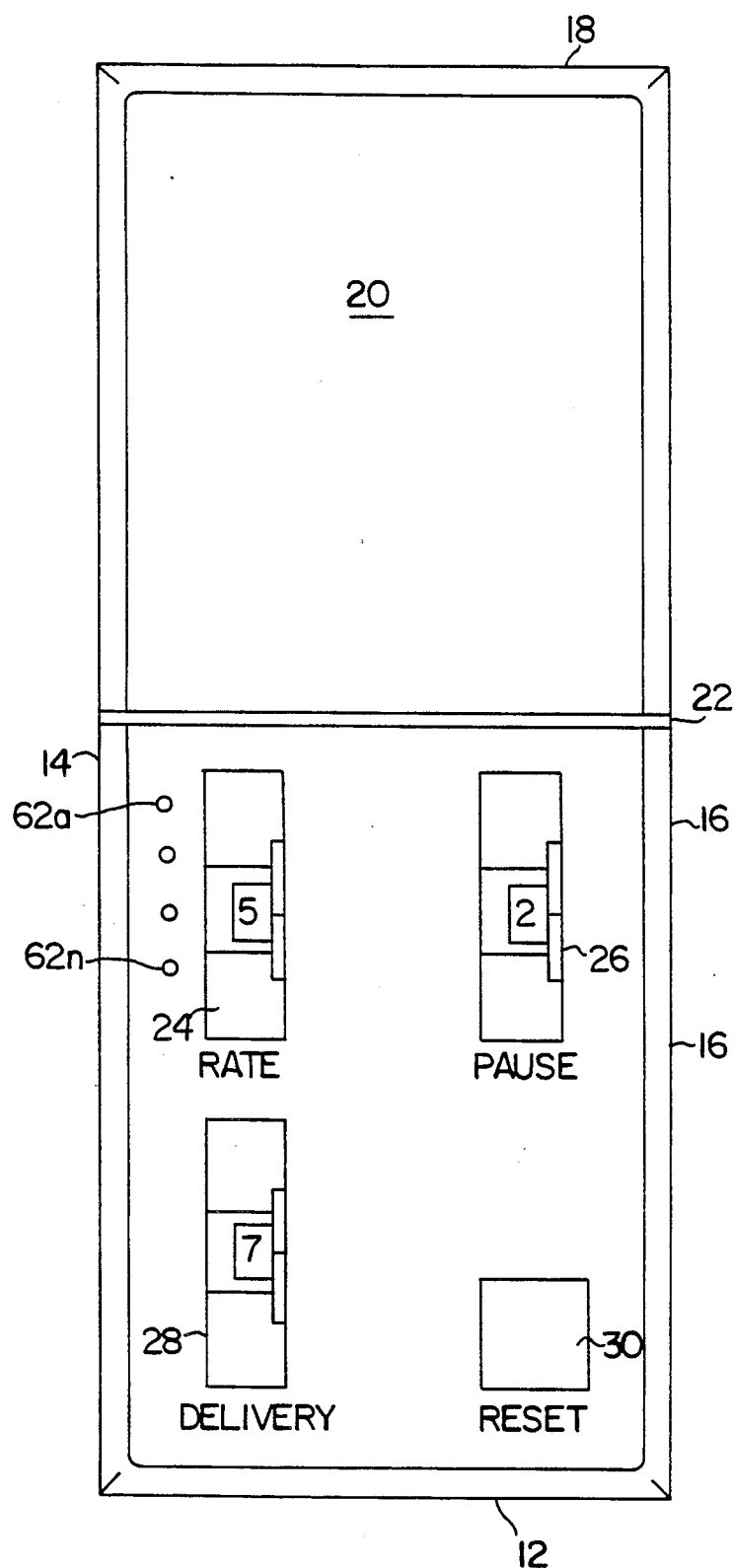
FIG. 9A illustrates a front view of the panel with thumb wheel switches.

FIG. 9A illustrates a front view of the panel 21 with the thumb wheel switches 24, 28 and 26 for dialing in the rate, the delivery, the pause, and a master reset button 30. All numerals correspond to those elements previously described. These switches program the hardware logic.

Figure 9B:
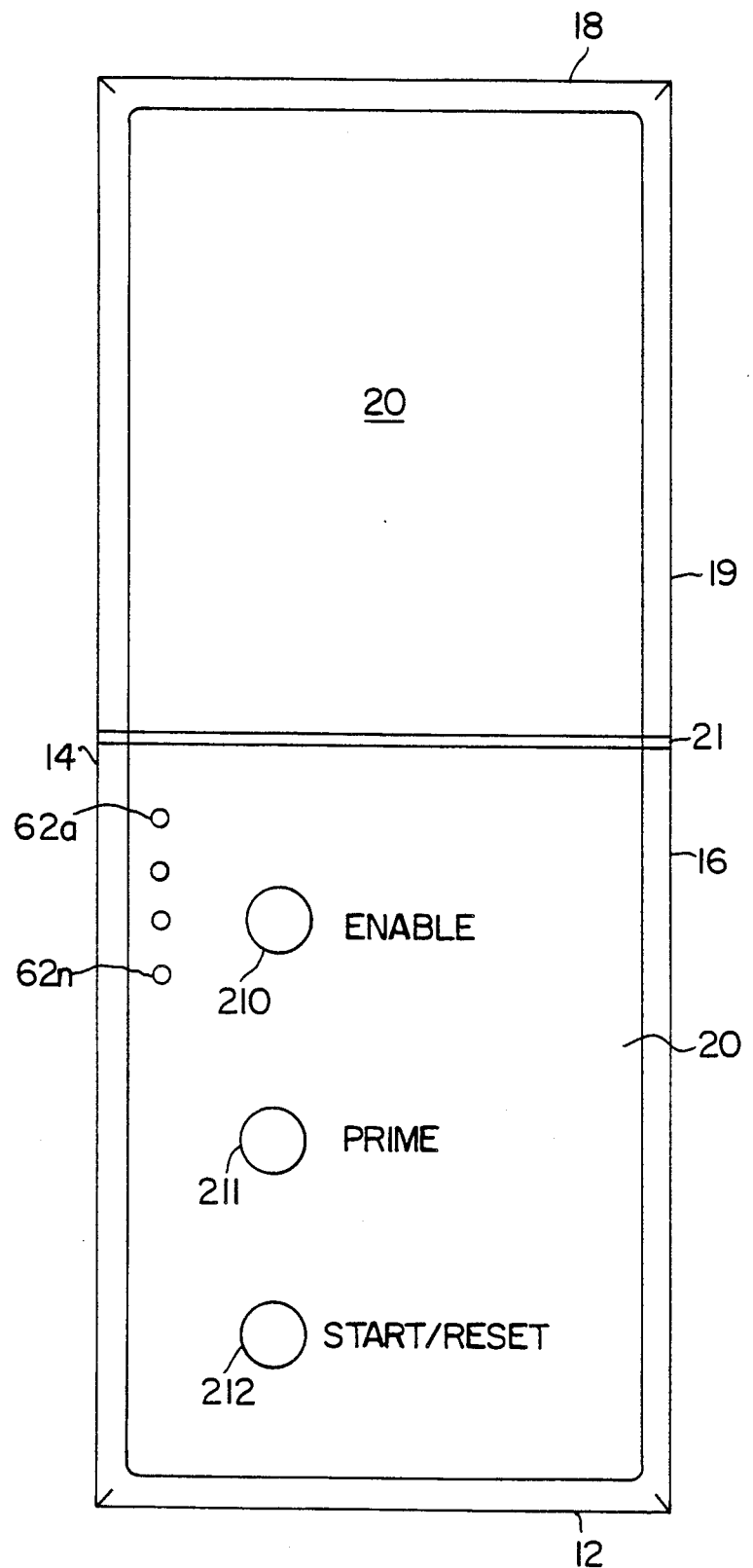
FIG. 9B illustrates a front view of the panel for tPA specific application.

FIG. 9B illustrates a front view of the front panel 21 as used for tPA specific control and where all numerals correspond to those elements previously described. Included are an enable switch 210, a prime switch 211 and a start/reset switch 212. These switches program the hardware logic.

Figure 10:
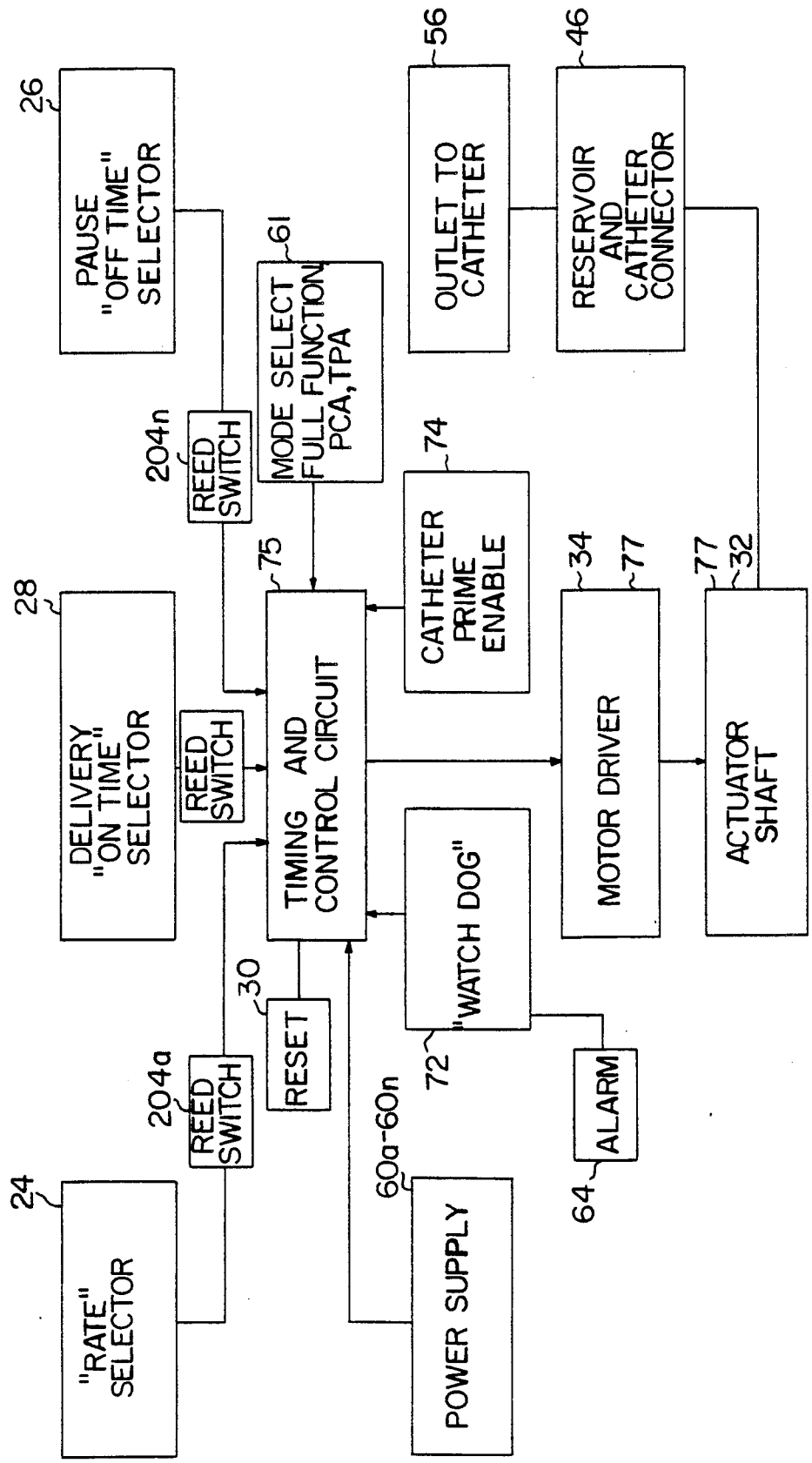
FIG. 10 illustrates a block diagram of the control circuitry.

FIG. 10 illustrates a block diagram of control circuitry where switches 24, 28 and 26 through a digital circuit control the advancing screw shaft 32 according to the selection of the rate, delivery and pause. All numerals correspond to those elements previously described. This includes preprogramming in a cradle 200 of FIG. 12 to prevent user/patient from altering the program as the pump programmed in the cradle cannot be reprogrammed outside of the same cradle. A "catheter prime" function circuit 74 is provided to cause the pump to run on an increased rate to prime the catheter. A "watch dog" circuit 72 is provided to prevent runaway operation or any other undesirable operation.

Figure 11:
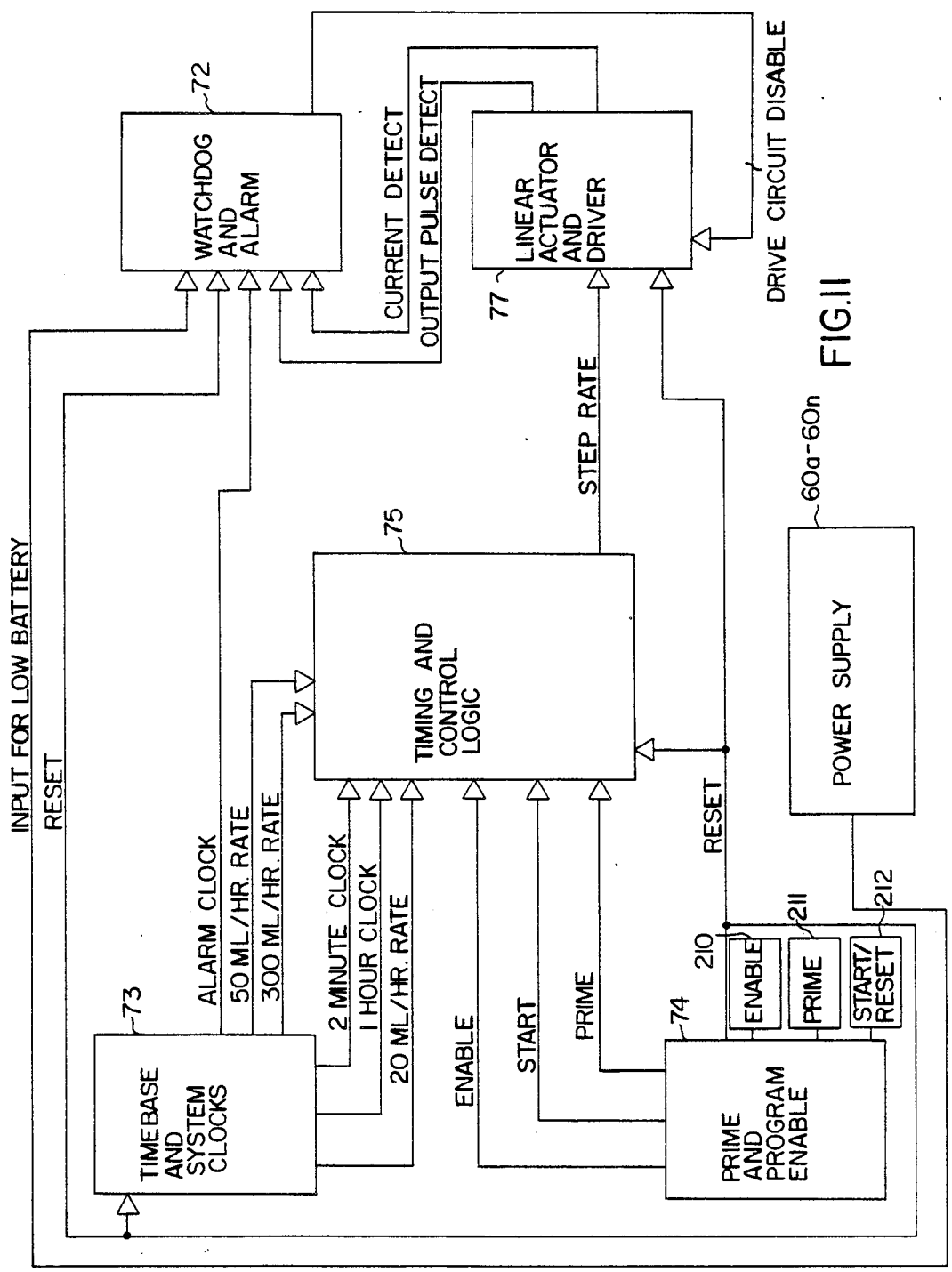
FIG. 11 illustrates a tPA circuit block diagram.

FIG. 11 illustrates a block diagram of the circuits for tPA operation. The electronic control and electromechanical drive circuits are separated into six functional blocks consisting of: the timebase and system clock section 73; prime and program enable 74; timing and control 75; watchdog and alarm 72; linear actuator and driver 77; and power supply 60a-60n.

The timebase logic 73 consists of a 32 kHz crystal oscillator tuned with and enabled by two CMOS inverters, two capacitors, and two resistors that are connected to provide a CMOS compatible square wave output of 32 kHz. The 32 kHz is then run through CMOS counters and logically "anded" to provide the rate clocks and time interval clocks necessary to the control logic. The timebase section also provides a reference clock for the alarm section used in establishing a window compare of controlled rate to actual rate in case of system failure.

The Prime and Program Enable section 74 consists of three mechanical switches 210, 211 and 212, as illustrated in FIG. 9B, that when pressed in the proper sequence initiate the catheter prime, or program initialization logic in the control section for the tPA mode of pump operation. This section also contains the LED indicators 62a-62n and their drivers to indicate system failure, catheter occlusion, and normal operation.

The Timing and Control Logic section 75 takes the clocks and rate signals, the enable/prime/start signals, and uses them to provide the correct step rate to the linear actuator and driver section 77 at the correct time. It does this using a series of CMOS D-Latches clocked along by the Enable and Prime switches 210 and 211 being pressed causing the 300 ml/hr rate to be on for catheter priming. Next the Enable and Start switches 210 and 212 are pressed starting the two minute delivery period which gates the 300 ml/hr rate clock to the linear actuator driver circuit. At this point the logic is committed to finish the designed-in sequence with the 50 ml/hr gated at the end of two minutes and lasting for 58 minutes. After one hour from starting the device the 20 ml/hr rate clock is enabled and allowed to run the linear actuator out to the end of its travel.

The Watchdog and Alarm section 72 contains three status indicators, an occlusion alarm, circuit failure/low battery alarm, and normal operation. Each with an audible, as well as visual LED 62a-62n indication of its operation. In the case of occlusion, as the reservoir collapses towards its final dimension, the occlusion alarm will sound and shut down the device. This alarm will also shut off the device if the catheter is accidentally kinked or any other flow obstruction is encountered. This alarm is resettable by pressing the Enable and Start switches 210 and 212 in the tPA mode of operation after the occlusion is cleared, but will immediately trigger again if the reservoir 46 is completely collapsed. In the general purpose pump, starting is via a push button switch and for priming the thumbwheel rate switch 24 set to maximum rate. If a clearable obstruction was encountered, resetting by pressing the Enable/Start switches 210 and 212 will restart the therapy from the point from which it stopped. The circuit failure/low battery alarm turns on when the expected rate does not match the actual rate, high or low, or when the end of effective battery 60a-60n is at an end. When the Failure/Low battery alarm occurs, the power supply to the drive is cut off by an FET switch insuring total and absolute shut down of all logic involved with driving the digital linear actuator motor 34. The normal operation indicator is on (flashes) when the fourth step in the digital linear actuator more 34 sequence occurs, or more simply, every fourth rate pulse.

The Linear actuator and driver section 77 includes the drive transistors for each actuator winding, current limiting and suppression resistors, suppression diodes, and the sequencing logic to operate the digital linear actuator motor 34 that drives the advancing screw shaft 32. The sequencing circuit is clocked at the rate enabled by the control logic and delivers the sequenced on/off switching of the drive transistors that in turn energize the windings of the motor 34. This circuit provides bi-directional control of the motor to facilitate testing.

The power supply 60a-60n consists of a plurality of batteries that supply approximately 1200 milliampere hours. This section also has a large polarized tantalum capacitor, 200 micro farads at 15 volts, to help reduce spiking effects by loads induced by the actuator motor.

Figure 12:
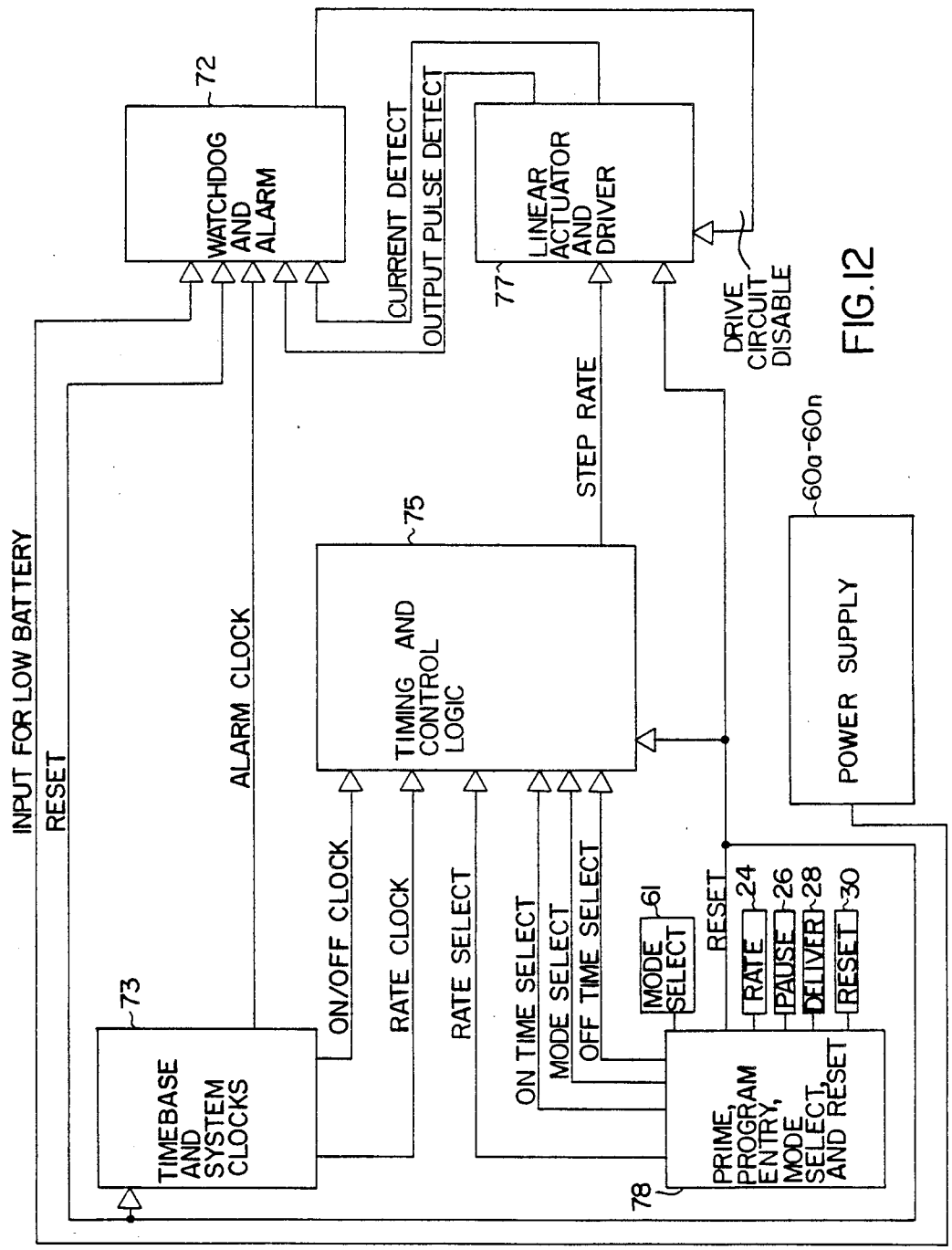
FIG. 12 illustrates a PCA and general purpose block diagram.

FIG. 12 illustrates a block diagram of the circuits for PCA and general purpose operation. The electronic control and electro-mechanical drive circuits are separated into six functional blocks consisting of: the timebase and system clock section 73; prime, mode select program and reset 74; timing and control 75; watchdog and alarm 72; linear actuator and driver 77; and, power supply 60a-60n.

The timebase logic 73 consists of a 32 kHz crystal oscillator tuned with and enabled by two CMOS inverters, two capacitors, and two resistors that are connected to provide a CMOS compatible square wave output at 32 kHz. The 32 kHz is then run through CMOS counters to provide the rate clock used in the control logic for establishing step rate, and logically "and" to provide time interval clocks necessary for on and off programming. The timebase section also provides a reference clock for the alarm section used in establishing a window compare of controlled rate to actual rate in case of system failure.

The prime, mode select, program and reset section 78 includes mechanical switches 61, 24, 26, 28 and 30 that when set or pressed in the proper sequence initiate the catheter prime and program logic in the control section. The switch selections determine the delivery rate and on/off time intervals required to fulfill a desired therapy. Mode switching is accomplished using a switch array set up in a binary configuration that presents to the control logic a pattern it decodes for establishing a desired mode. The modes can be general, somewhat specific, or specific in nature allowing all features of the device to be utilized. The most general mode selection allows the device to be programmed and reprogrammed by the user over the entire life of the pump. The more specific modes, as in the case of Patient Controlled Analgesia (P.C.A.), give the clinician control of programming. Finally, very specific modes where a fixed regimen is established and must be implemented in an exact way.

This section also contains the audible and visible indicators and their drivers used to indicate system failure, catheter occlusion, and normal operation. A reset switch is also provided for program initialization and occlusion alarm resetting.

The timing and control logic 75 uses the clock and rate signals, and the program/prime/reset signals, to provide the correct step rate and on/off time intervals to the linear actuator and driver section at the correct time. It does this using programmable counters, a mode select decode circuit, and priming circuit. The programmable counters take the interval clock and the basic rate clock from the timebase section and divide them per the program switch setting, producing the control signals that regulate interval timing and motor rate. The mode decode circuit uses the binary word from the mode select switches. It translates the word into various enable signals, depending on the switch settings, that the control logic then uses to establish the level of intended use.

For instance, if full functions are desired at all times regardless of the user, the device will allow itself to be reprogrammed at any time. In the case where limited access to programming is desired, the control logic will decode the mode select setting and enable a circuit that will allow programming to occur only while the device is in its programming cradle. The cradle contains magnetic material that is polarized, and while the device is in place on the cradle, magnetic switches are turned on enabling a rate and time interval to be programmed. Once removed from the cradle, magnetic switches are disabled, thus the rate and time interval of the device cannot be changed. However, at the end of the programmed interval, which is the sum of the time on and time off select switches, the program may be restarted by the user pressing the reset switch. When specific and consistent therapy is required, the device has an area that can be tailored to provide a given series of on and off times and rates.

Priming of the catheter is controlled in this section 74 with rate switch 24 set to maximum rate and reset button 30 pressed. In case of tPA-specific pump "prime" and "enable" switch 210 and 211 are pressed and held until fluid is seen by the clinician at the catheter's end.

The watchdog and alarm section 72 contains status indicators, an occlusion alarm, circuit failure/low battery alarm, and normal operation, each with an audible, as well as visual indicator. In the case where back pressure increases as the reservoir collapses, the occlusion alarm will sound and shut off the device. This alarm will also shut off the device if the catheter is accidentally kinked or some other obstruction is encountered. This alarm is resettable by pressing the rest switch after the occlusion is cleared, but will trigger again if the reservoir is completely collapsed or catheter is still obstructed. When the obstruction is cleared, resetting will restart the therapy from the point it stopped at.

The circuit failure/low battery alarm turns on when the expected rate does not match the actual rate, high or low, or when effective battery life is at an end. When the Failure/Low battery alarm occurs, the power supply to the drive is cut off by a FET switch insuring total and absolute shut down of all logic involved with driving the actuator. The normal operation indicator is on when the forth step in the actuator motor sequence occurs, or more simply, every forth clock pulse.

The digital linear actuator driver section 77 includes the drive transistors for each actuator winding, current limiting and suppression resistors, suppression diodes, and the sequencing logic to operate the actuator motor that drives the linear actuator. The sequencing circuit is clocked at the rate enabled by the control logic and delivers the sequenced on/off switching of the drive transistors that in turn energize the windings of the motor. This circuit provides bidirectional control of the motor to facilitate testing.

The 6 V power supply 60a-60n consists of a multitude of batteries that supply approximately 200 percent of required capacity. This section also has a large polarized tantalum capacitor, grater than 200 micro farads at 15 volts, to help reduce spiking effects by loads induced by the actuator motor.

Figure 13:
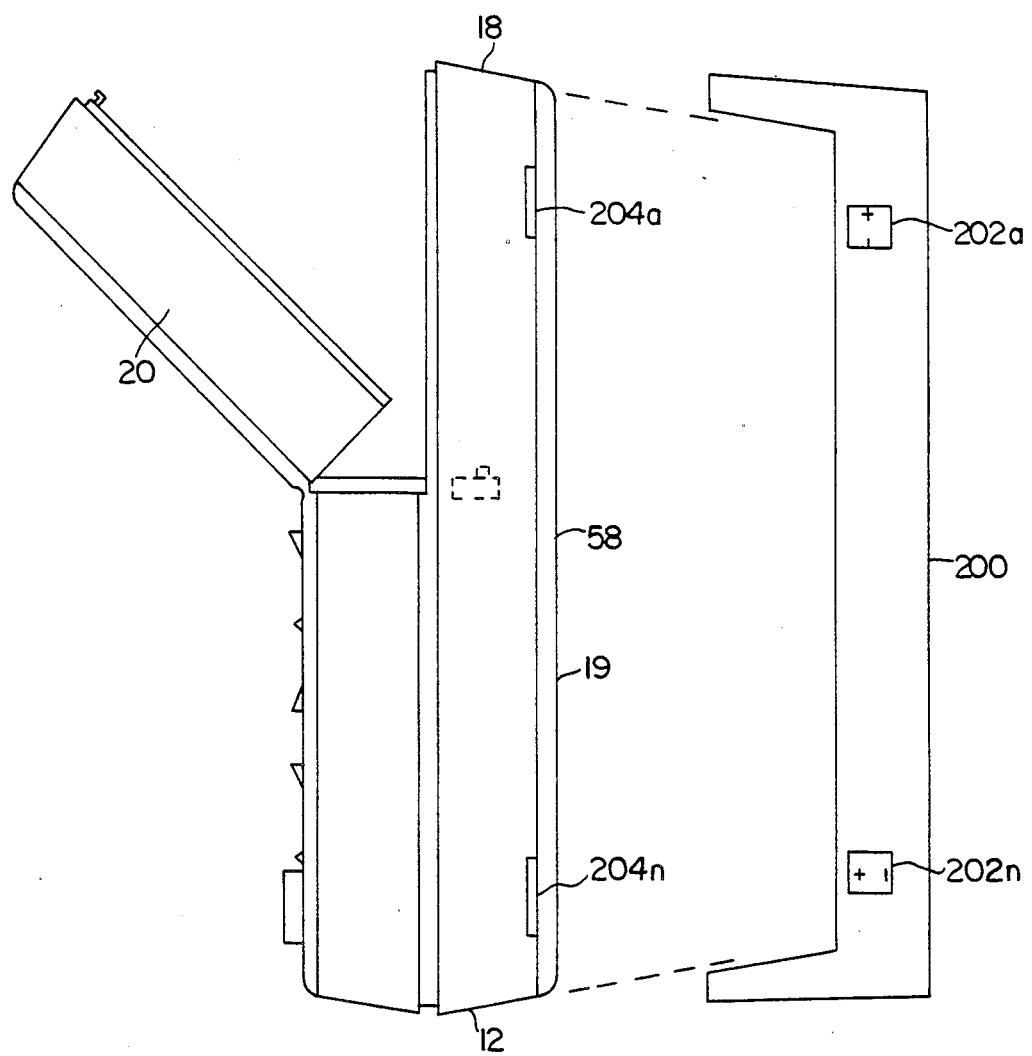
FIG. 13 illustrates a programming cradle.

FIG. 13 illustrates a base cradle 200 with a plurality of magnets 202a-202n which actuate specifically oriented reed switches 204a-204n. This provides control of the unit, in that the unit cannot be programmed if such is so desired unless the unit is on the specific base with the specific oriented magnets corresponding to that particular pump or series of pumps.

Various modifications can be made to the present invention without departing from the apparent scope hereof.

We claim:

1. A pump comprising:
   a. a reservoir including folding bellows and a threaded aperture in a top of said reservoir for receiving a drug;
   b. a catheter connector with threads for screwing into said threaded aperture of said reservoir;
   c. a housing for respectively receiving said reservoir and said connector and including a door;
   d. an actuator motor in said housing and including an upwardly advancing shaft powered by the actuator motor and which provides force at one end of the reservoir to compress said reservoir; and,
   e. control means connected between a power supply and said actuator motor for controlling operation of said actuator motor.

2. Pump of claim 1 wherein each fold of said bellows is compressed at the same rate when a force is applied by said shaft.

3. Pump of claim 1 including teeth means about said reservoir aperture and on said catheter connector to lock said catheter connector to said reservoir.

4. Pump of claim 3 wherein said means of locking said catheter connector to said reservoir includes N+1 flexible teeth on said catheter connector and N fixed teeth on said reservoir whereby the teeth ratchet over each other providing that the catheter connector cannot be unscrewed.

5. Pump of claim 1 including locking means for said door.

6. Pump of claim wherein said control means includes means to control the rate at which said actuator motor linearly advances said shaft, the time said actuator motor is on, and the time said actuator motor is off.

7. An infusion pump of claim 6 including means to select different modes of drug delivery.

8. Pump of claim 7 wherein said mode is tPA.

9. Pump of claim 7 wherein said mode is PCA.

10. Pump of claim 7 wherein said mode is general purpose.

11. Pump of claim 6 wherein said selection to select different modes of operation of said control means is located inside the housing.

12. Pump of claim 11 where there is a means of setting the rate of the actuator motor, the time on of the actuator motor and the time off of the actuator motor, and a reset switch which are all accessible on the outside of the infusion pump housing.

13. Pump of claim 1 further including:
   a. a cradle for said pump housing, said cradle including a plurality of magnets; and,
   b. a plurality of magnetically activated switches in said housing connected to said control means whereby said switches must be closed by said magnets for programming one mode of said control means when said housing engages in said cradle.

14. Collapsible drug reservoir comprising:
   a. a container of substantially rectangular shape with a plurality of side wall bellows therein including a septum in a bottom of said container; and,
   b. a threaded aperture with connector means in a top of said aperture and a locking means about said threaded aperture.

15. In combination, a drug reservoir and connector comprising:
   a. a container with a plurality of side wall bellows therein, a threaded aperture in a top of said container, a locking means about said aperture; and, b. a catheter connector with threads and a corresponding locking means about said connector to engage with said aperture locking means.

16. Combination of claim 15 wherein said locking means are n locking teeth, and wherein either of said locking means includes n+1 teeth with respect to n teeth of said other locking means.

17. Combination of claim 15 wherein said locking means provides sterility between said reservoir and said connector.

18. Combination of claim 15 wherein said connector includes a breakaway top.

19. Drug pump comprising:

a. a driver and motor means including means for linearly advancing a shaft upwardly;
b. a reservoir including a plurality of bellows, means for accepting said shaft and an aperture means;
c. catheter connector means to engage with said aperture means to a catheter;
d. hardware discrete logic control means connected between said motor means and a power supply means; and,
e. switch means connected to said hardware discrete logic control means to program said hardware discrete logic control means.

* * * * *